United States Patent [19]

Frederick et al.

[11] Patent Number: 4,568,366
[45] Date of Patent: Feb. 4, 1986

[54] IN-LINE FILTER

[75] Inventors: Warren P. Frederick, Wonderlake; William Rudzena, McHenry; Albert Stone, Buffalo Grove, all of Ill.

[73] Assignee: Baxter Laboratories, Inc., Deerfield, Ill.

[21] Appl. No.: 527,932

[22] Filed: Aug. 30, 1983

[51] Int. Cl.⁴ .......................................... B01D 19/00
[52] U.S. Cl. ...................... 55/159; 210/436; 604/406
[58] Field of Search ............ 55/159, 36, 16, 158; 210/436, 455, 321.1, 433.2; 422/45, 48; 604/126, 406,

[56] References Cited

U.S. PATENT DOCUMENTS

| | | | |
|---|---|---|---|
| 2,675,000 | 4/1954 | Ford | 128/214 |
| 2,704,544 | 3/1955 | Ryan | 128/214 |
| 3,471,019 | 10/1969 | Trasen et al. | 210/94 |
| 3,503,515 | 3/1970 | Tomsic | 210/321 |
| 3,612,282 | 10/1971 | Cheng | 210/321 |
| 3,650,093 | 3/1972 | Rosenberg | 55/159 |
| 3,660,281 | 5/1972 | Tober | 210/651 |
| 3,702,658 | 11/1972 | McNamara et al. | 210/321 |
| 3,730,959 | 5/1973 | Horres, Jr. et al. | 264/263 |
| 3,760,949 | 9/1973 | Carey et al. | 210/321.1 |
| 3,854,907 | 12/1974 | Rising | 55/159 |
| 3,856,683 | 12/1974 | Parr | 210/336 |
| 3,884,814 | 5/1975 | Vogt et al. | 210/321 |
| 3,970,084 | 7/1976 | Raines et al. | 128/214 C |
| 3,978,857 | 9/1976 | McPhee | 128/214 R |
| 4,190,426 | 2/1980 | Ruschke | 55/185 |
| 4,238,207 | 12/1980 | Ruschke | 55/159 |
| 4,267,053 | 5/1981 | Hashino et al. | 210/650 |
| 4,306,973 | 12/1981 | Ishikawa | 210/336 |
| 4,318,812 | 3/1982 | Vcelka | 210/323.2 |
| 4,378,981 | 4/1983 | Otstot et al. | 55/158 |
| 4,401,567 | 8/1983 | Shindo et al. | 210/500.2 |

FOREIGN PATENT DOCUMENTS

| | | |
|---|---|---|
| 831779 | 1/1970 | Canada . |
| 5348392 | 5/1978 | Japan . |
| 5349885 | 5/1978 | Japan . |

OTHER PUBLICATIONS

"Evaluation of a Prototype Air-Venting Inline Intravenous Filter Set", Robert Rapp et al., *American Journal of Hospital Pharmacy*, vol. 32, Dec. 1975, pp. 1253-1259.

Primary Examiner—Charles Hart
Attorney, Agent, or Firm—Paul C. Flattery; John P. Kirby, Jr.; Bradford R. L. Price

[57] ABSTRACT

An in-line set filter for parenteral solution sets and the like which comprises a tubular housing having first and second ends. A bundle of filter tubes is positioned within the housing, the filter tubes preferably being folded so that all ends of the filter tubes occupy a single zone in communication with the first housing end. The zone is filled with potting compound with the filter tube ends communicating through the potting compound and open to the exterior. A flow access port is laterally positioned in a side wall between the second end and the potting compound but closer to the potting compound. The second end defines an open aperture occluded by a porous hydrophobic filter to permit venting while preventing loss of aqueous liquid.

16 Claims, 2 Drawing Figures

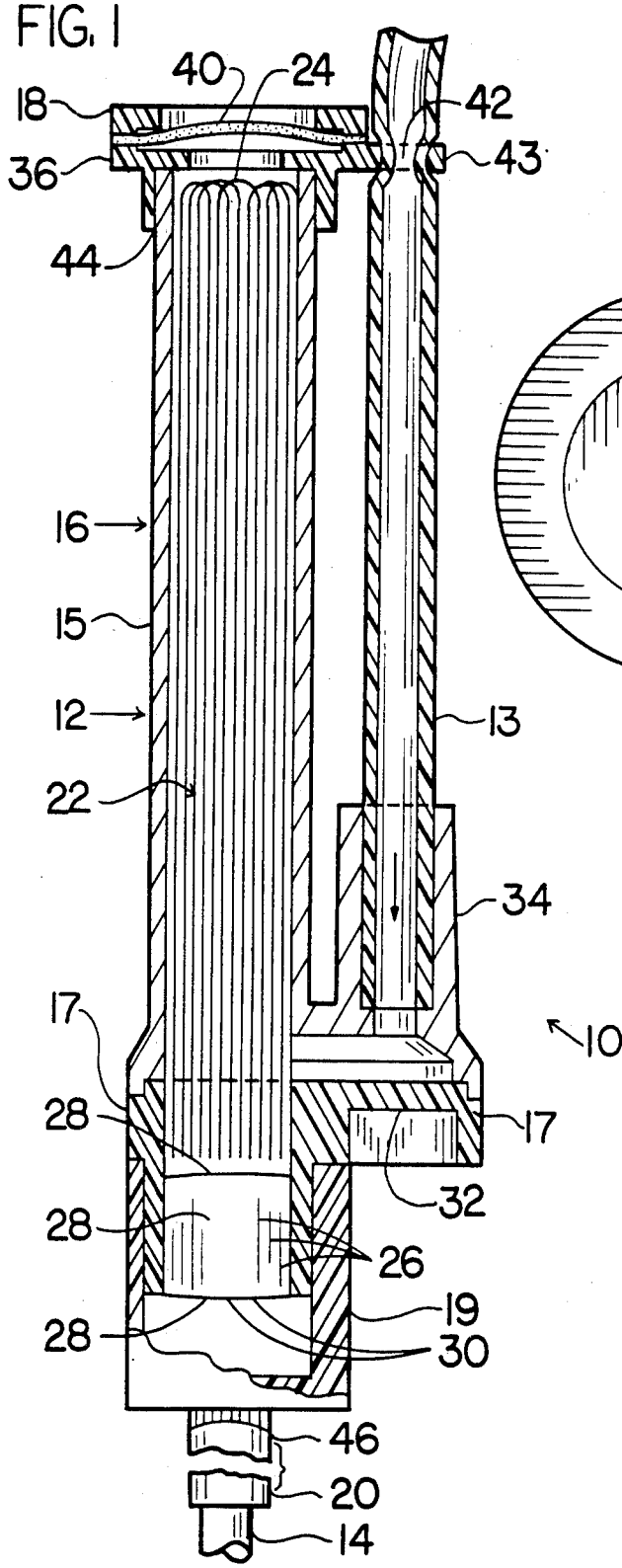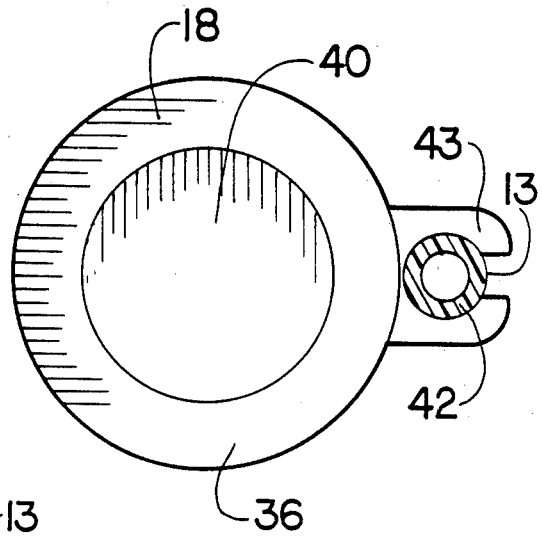

IN-LINE FILTER

TECHNICAL FIELD AND PRIOR ART

This application relates to an in-line filter for parenteral solution sets and other uses, particularly in the medical field in which a small filter can have high capacity due to the use of tubular porous filter membranes.

In Ishikwa U.S. Pat. No. 4,306,973 a filter for a medical liquid dispenser is provided with filter fibers folded back on themselves so that all of the open ends are in a single position and surrounded and sealed with a partition element.

Tober U.S. Pat. No. 3,660,281 discloses a permeation separation apparatus for use in reverse osmosis, for example, having folded tubular membranes in a manner similar to the previously cited patent, in a housing adapted for cross flow so that solution for processing passes into the housing and out of the housing across the filter membranes.

In accordance with this invention, the filter device is preferably of the folded tubular membrane type in a tubular housing in which the desired high capacity filtration provided by tubular filter membranes is combined with means for facilitating the priming of the filter so that air bubbles are not trapped in the filter. After the filter has become wetted, air bubbles will not readily pass through it. While hydrophobic vents for filters are well known in the filter art, for example, as shown in Ruschke U.S. Pat. No. 4,190,426, the structure of the filter of this application and its vent provide expedited use in effective priming without the retention or trapping of air bubbles in the system, coupled with the desired high filtering capacity of the filter system of this invention.

DESCRIPTION OF THE INVENTION

In accordance with this invention, an in-line set filter is provided which comprises a tubular housing having first and second ends. A bundle of filter tubes is positioned within the housing. In the preferred embodiment the filter tubes are folded so that all ends of the filter tubes occupy a single zone in open communication with, and preferably near, the first housing end.

The zone is filled with potting compound surrounding the tubes and adhering to an inner wall of the housing, with the filter tube ends communicating through the potting compound and open to the exterior near the first housing end. A flow access port laterally positioned in a side wall of the housing is at a position closer to the first end than the second end, but is positioned between the second end and the potting compound.

The second end defines an open aperture which is occluded by porous hydrophobic filter membrane means to permit passage of gas while preventing passage of aqueous liquids passing through the filter system.

As stated above, the filter of this invention is intended for use in combination with the medical fluid administration set or the like. The first end and flow access port may be connected to set tubing. The remainder of the set may be of any desired design, many conventional designs of such sets being well known and in commercial use. Specifically, the filter of this invention may replace present commercial design filters on presently available administration sets.

The filter tubes used herein are a polymeric material and are typically made of porous polyolefin, for example porous polyethylene, and exhibit a pore size of about 0.2 micron to be bacteria blocking.

The filter tubes may preferably have outer diameters of less than about 0.01 inch to about 0.02 inch, and wall thickness of about 0.001 to 0.005 inch. Also, the filter tubes may be impregnated with a surfactant to facilitate the flow of aqueous liquid therethrough, or rendered hydrophillic in some other way, such as by acid treatment or plasma treatment.

DESCRIPTION OF THE DRAWINGS

In the drawings, FIG. 1 is an elevational view taken partly in section of a portion of a conventional parenteral solution set showing one embodiment of the filter of this invention in partial longitudinal section.

FIG. 2 is an enlarged top plan view of the filter of FIG. 1.

DESCRIPTION OF SPECIFIC EMBODIMENT

Referring to the drawings, a portion of a set 10 is disclosed in FIG. 1 being made of a filter 12 which is connected at the two ends of its flow path with flexible plastic tubing 13, 14 which communicates to other portions of the set in conventional manner.

Filter 12 comprises a tubular housing 16 having first and second ends 20, 18. The housing 16 shown is constructed of three molded plastic pieces. These are an upper housing 15, an intermediate portion 17 and a lower end cap 19. However, the housing 16 may be made in one piece.

A bundle of filter tubes 22 is positioned within housing 16, with the bundle of filter tubes being folded as shown at 24 so that all ends 26 of the filter tubes occupy a single zone in communication with the first housing end 20. To minimize the size of the filter 12 the tube ends 26 are near the housing end 20 but this is not critical. "Near" includes adjacent.

As shown, the ends of filter tubes 26 and the zone which they occupy may be filled with potting compound 28 surrounding the tubes and adhering to an inner wall of housing 16 so that the filter tube ends communicate through the potting compound and open to the exterior near the first housing end 20 with the open bores being at location 30. The potting compound may be polyurethane but other known potting compounds will work, such as epoxies, hot melts and silicone. As an alternative structure, the filter tubes 26, instead of being folded, may be straight tubes having closed ends opposite the open ends in the potting compound. However, this involves the additional step of sealing closed one end of each filter tube 26.

A flow access port 32 is laterally positioned in a side wall of housing 16. The access port 32 is positioned between second end 18 and potting compound 28, at a position closer to the potting compound 28 than the second end 18 and preferably closer to the first end 20 than the second end 18. Access port 32 may define a tubular section 34 outside of housing 16 which is parallel to the housing and which serves as a site for attachment of flexible set tubing 13.

Second end 18 of housing 16 defines attachment 36 which may be insert molded as a frame around porous hydrophobic filter 40. The hydrophobic filter 40 may be of any common known design. For example, in the preferred embodiment the filter 40 is a commercially available hydrophobic filter membrane which is a conventional hydrophobic filter to prevent airborne contamination. The filter may be in the range of, for example, 0.02 to 0.2 micron. In the preferred embodiment, the hydrophobic filter 40 is a 0.22 micron bacteria blocking hydrophobic filter. The parts of the filter 40 are sealed together by the insert molding process so that the combined structures 36, 40 may then be conventionally sealed at annular seal section 44 to the remainder of housing 16.

As the result of this, the filter of this invention, with attached tubing 13, 14 of a set 10, may receive liquid flowing through side port 32 into flow contact with the outside of the filter tubes of bundle 22. The bore of housing 16 may become partially filled with such liquid with filtering action taking place as the liquid flows through the pores of the filter tubes in the bundle 22. The filtered liquid then flows through the bores of the filter tubes of bundle 22 out of the ends 30 of such filter tubes through tubing 14 for continued passage through the set, with the filtered material being retained on the outside surfaces of the filter tubes of bundle 22.

Filter 12 is typically retained in the upright position as shown in FIG. 1. Accordingly, any gas bubbles inside of housing 16 can easily pass through hydrophobic, porous membrane 40 to be vented, while aqueous liquid cannot so pass through the hydrophobic filter 40. When 0.22 micron hydrophobic filter is used for filter 40, bacteria cannot enter the system.

Also the filter of this invention exhibits highly facilitated priming. The filter is typically initially dry, and as liquid enters the bundle through said port 32, the wetted filter tubes can no longer pass air. However, any remaining air which is entrapped within housing 16 can be easly vented through hydrophobic, porous membrane 40.

The individual filter tubes of bundle 22 may be made of porous polyethylene having an inner diameter of 0.011 inch, an outer diameter of 0.015 inch, and a nominal bacteria-blocking pore size of 0.22 micron. Typically, about 32 filter tubes may be used, each folded so that there are 64 ends in the potting compound 28.

It may also be desired for the filter tubes to carry, particularly on their inner surfaces, but also optionally on their outer surfaces and within their pores, a surfactant to facilitate the flow of aqueous liquid therethrough. A specific example of surface active agent of this invention which is preferred is a mixture of monoesters of sorbitan with capric, lauric, myristic, palmitic, and/or oleic acids. As a specific example, the mixture may include the following typical weight percentages of monoesters: sorbitan caprate, 1.1 percent; sorbitan laurate, 43.5 percent; sorbitan myristate, 27.8 percent; sorbitan palmitate, 19.2 percent; and sorbitan oleate, 8.4 percent. However, other analogous esters may be used, pure or mixed, preferably monoesters of carbohydrates such as sorbitan, glucose, fructose, or other metabolizable carbohydrates of preferably 5 to 6 carbon atoms. A surfactant, and particularly the ones described above, facilitates the passage of aqueous liquids through the porous filter tubes even when made of a hydrophobic material such as polyethylene.

Aperture 42 defined in projecting member 43 may serve as a passageway for tube 13 to pass through, stabilizing filter 12 relative to tube 13, to assist it to occupy a vertical position for good venting through porous hydrophobic membrane 40.

The lower end cap 19 may be made of molded plastic and provides a manifold distribution system between the ends 30 of bundle of filter tubes 22 and communicating tubing 14 which may be solvent sealed into tubular segment 46 of end cap 19. Lower end cap 19, intermediate portion 17 and upper housing 15 may be sealed together in conventional manner as shown.

The filter of this invention exhibits greatly improved filter capacity similar to that of a depth filter, and better and much superior to the prior art membrane filters which have been used in the past on parenteral solution sets and the like. At the same time the filter can vent with great ease, and thus can be easily primed without compromise of the sterility of the interior of the filter. Typically the filter is of small size being typically 2 to 4 inches in length, but despite this exhibits the high capacity and the other desired features mentioned above.

The above has been offered for illustrative purposes only, and is not intended to limit the scope of the invention of this application, which is as defined in the claims below.

That which is claimed is:

1. A filter which comprises a tubular housing having first and second ends, said first end being adapted for connection to downstream tubing of a medical fluid administration set, a bundle of filter tubes positioned within said housing, said filter tubes being folded so that all ends of said filter tubes occupy a single zone in open communication with the first housing end, said zone being filled with potting compound surrounding said tubes and adhering to an inner wall of the housing with the filter tube ends communicating through said potting compound and open to the exterior of said housing at the first housing end, a flow access port adapted for connection to upstream tubing of a medical fluid administration set, said flow access port including a tubular section which is in parallel juxtaposition to said housing, said flow access port being laterally positioned in a side wall of said housing between said potting compound and said second end, at a position closer to said potting compound than to said second end, said second end defining an open aperture occluded by porous, hydrophobic filter means to permit passage of gas while preventing passage of aqueous liquids, said tubular housing being adapted for retention in the upright position by said tubular section when fluid flows therethrough so that gas bubbles can easily pass through said porous hydrophobic filter means.

2. The filter of claim 1, further comprising a member projecting from said filter for securement to the tubing upstream of said flow access port, said projecting member thereby stabilizing said filter in a vertical, upright position.

3. The filter of claim 1 in which said filter tubes are made of porous polyethylene.

4. The filter of claim 3 in which pore size of said filter tubes is sufficiently small to block bacteria.

5. The filter of claim 3 in which said filter tubes have outer diameters of no more than 0.02 inch and wall thicknesses of 0.001 to 0.005 inch.

6. The filter of claim 5 in which said filter tubes carry a surfactant to facilitate the flow of aqueous liquid therethrough.

7. The filter of claim 6 in which said surfactant is a mixture of monoesters of sorbitan.

8. The filter of claim 1 in which said hydrophobic filter means is a membrane filter.

9. The filter of claim 8 in which said hydrophobic membrane filter is a 0.22 micron bacteria blocking filter.

10. The filter of claim 1 in which said potting compound comprises polyurethane.

11. A filter which comprises a tubular housing having first and second ends, a bundle of polyethylene filter tubes positioned within said housing, said filter tubes being folded so that all ends of said filter tubes occupy a single zone in open communication with the first housing end, said zone being filled with potting compound surrounding said tubes and adhering to an inner wall of the housing with the filter tube ends communicating through said potting compound and open to the exterior of said housing at said first housing end, a flow access port laterally positioned in a side wall of said housing between said potting compound and said second end, at a position closer to said potting compound than to said second end, said flow access port having a tubular postion in parallel juxtaposition to said housing, said second end defining an open aperture occluded by porous hydrophobic filter means to permit passage of gas while preventing passage of aqueous liquids, said filter being in combination with a medical fluid administration set, the first end and flow access port being connected to set tubing, said tubular housing being adapted for retention in the upright position by said tubular portion when fluid flows therethrough, so that gas bubbles can easily pass through said porous, hydrophobic filter means, said filter tubes having a pore size small enough to block bacteria, outer diameters of no more than 0.02 inch, and wall thicknesses of 0.001 to 0.005 inch, said filter tubes carrying a surfactant to facilitate the flow of aqueous liquid therethrough.

12. The filter of claim 11, further comprising a member projecting from said filter for securement to the tubing upstream of said flow access port, said projecting member thereby stabiliziang said filter in a vertical, upright position.

13. The filter of claim 11, in which said hydrophobic filter means is a membrane filter.

14. The filter of claim 13 in which said porous hydrophobic filter membrane has a pore size small enough to block bacteria.

15. A filter which comprises a tubular housing having first and second ends, said first end being adapted for connection to downstream tubing of a medical fluid administration set, a bundle of filter tubes positioned within said housing, one end of each filter tube occupying a single zone in open communication with the first housing end, said zone being filled with potting compound surrounding said tubes and adhering to an inner wall of the housing with each of said one filter tube ends communicating through said potting compound and open to the exterior of said housing at the first housing end, each of said filter tubes having an other, closed end opposite said one, opened, a flow access port adapted for connection to upstream tubing of a medical fluid administration set, said flow access port including a tubular section which is in parallel juxtaposition to said housing, said flow access port being laterally positioned in a side wall of said housing between said potting compound and said second end, at a position closer to said potting compound than to said second end, said second end defining an open aperture occluded by porous, hydrophobic filter means to permit passage of gas while preventing passage of aqueous liquids, said tubular housing being adapted for retention in the upright position by said tubular section when fluid flows therethrough, so that gas bubbles can easily pass through said porous hydrophobic filter means, said filter tube closed ends being closer than said filter tube open ends to said hydrophobic filter means.

16. The filter of claim 15, further comprising a member projecting from said filter for securement to the tubing upstream of said flow access port, said projecting member thereby stabilizing said filter in a vertical, upright position.

* * * * *